United States Patent
Napoletano et al.

(10) Patent No.: US 6,358,973 B1
(45) Date of Patent: Mar. 19, 2002

(54) BENZAZINE DERIVATIVES AS PHOSPHODIESTERASE 4 INHIBITORS

(75) Inventors: Mauro Napoletano, Milan; Gabriele Norcini, Vizzola Ticino; Giancarlo Grancini, Nova Milanese; Franco Pellacini, Milan; Gabriele Morazzoni, Lainate; Lorenzo Pradella, Cernusco sul Naviglio, all of (IT)

(73) Assignee: Zambon Group S.p.A., Vicenza (IT)

( * ) Notice: Subject to any disclaimer, the term of this patent is extended or adjusted under 35 U.S.C. 154(b) by 0 days.

(21) Appl. No.: 09/806,496

(22) PCT Filed: Oct. 10, 1999

(86) PCT No.: PCT/EP99/07302

§ 371 Date: Apr. 13, 2001

§ 102(e) Date: Apr. 13, 2001

(87) PCT Pub. No.: WO00/21947

PCT Pub. Date: Apr. 20, 2000

(30) Foreign Application Priority Data

Oct. 15, 1998 (IT) .......................... MI98A2216

(51) Int. Cl.$^7$ .................... C07D 40/06; A61K 31/47
(52) U.S. Cl. ................. 514/307; 546/139; 546/152; 514/314
(58) Field of Search ................ 514/307, 314; 546/152, 139

(56) References Cited

U.S. PATENT DOCUMENTS

| 5,455,252 A | 10/1995 | Wilhelm et al. | ............ 514/307 |
| 5,556,862 A | 9/1996 | Imai et al. | ................. 514/307 |

FOREIGN PATENT DOCUMENTS

| EP | 0 490 823 | 6/1992 |
| EP | 0 722 936 | 7/1996 |
| EP | 0 848 000 | 6/1998 |
| GB | 1199768 | 7/1970 |
| WO | WO 88/07041 | 9/1988 |
| WO | WO 97/04779 | 2/1997 |
| WO | WO 97/38977 | 10/1997 |
| WO | WO 88/07041 | * 9/1998 |
| WO | WO 99/32449 | 7/1999 |

OTHER PUBLICATIONS

Knabe et al, Chemical Abstracts, vol. 83, No. 21, Abstract 178765e, p. 548, Nov. 1975.*
Knabe et al, Chemical Abstracts, vol. 82, No. 24, Abstract 170629x, p. 512, Jun. 1975.*

* cited by examiner

Primary Examiner—Zinna Northington Davis
(74) Attorney, Agent, or Firm—Oblon, Spivak, McClelland, Maier & Neustadt, P.C.

(57) ABSTRACT

Compounds of formula I:

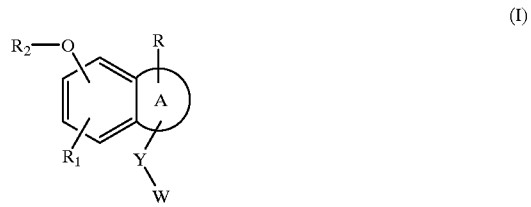

wherein A is a heterocycle containing a nitrogen atom and optionally saturated or unsaturated and optionally further substituted by an oxo group (=O); R is: hydrogen, cyano, $(C_{1-4})$alkoxycarbonyl, carbamoyl; optionally substituted $(C_{4-7})$-cycloalkyl, aryl or heterocycle; $(C_{1-8})$alkyl, $(C_{2-8})$alkenyl or $(C_{2-8})$alkynyl optionally branched and/or substituted by $(C_{4-7})$ cycloalkyl, aryl or heterocycle; aryloxy, heterocyclyloxy, aryl$(C_{1-4})$alkoxy, heterocyclyl$(C_{1-4})$alkoxy, amino substituted by one or two $(C_{1-4})$alkyl group(s), aryl-amino, heterocyclyl-amino, aryl$(C_{1-4})$alkyl-amino, or heterocyclyl$(C_{1-4})$alkylamino; Y is methylene or ethylene; W is an optionally substituted aryl or heterocycle; $R_1$ is hydrogen, $(C_{4-7})$cycloalkyl or a $(C_{2-8})$alkyl, $(C_{2-8})$alkenyl or $(C_{2-8})$alkynyl group optionally substituted by hydroxy, oxo, $(C_{4-7})$cycloalkyl, aryl or heterocycle, and optionally interrupted by one or more heteroatom(s) or heterogroup(s); $R_2$ is a $(C_{1-6})$alkyl or polyfluoro$(C_{1-6})$alkyl group; the N→O derivatives of the compounds of formula I and the pharmaceutically acceptable salts thereof. The compounds of formula (I) are PDE 4 inhibitors and may be used in compositions and methods involving PDE 4 inhibition.

19 Claims, No Drawings

BENZAZINE DERIVATIVES AS PHOSPHODIESTERASE 4 INHIBITORS

CROSS-REFERENCE TO RELATED APPLICATIONS

This application is a national-stage filing under 371 of PCT/EP99/07302, filed Oct. 10, 1999.

BACKGROUND OF THE INVENTION

1. Field of the Invention

The present invention relates to benzazine derivatives, to the pharmaceutical compositions containing them and to their use as phosphodiesterase 4 inhibitors.

2. Description of Related Art

Phosphodiesterases are a family of isoenzymes which constitute the basis of the main mechanism of cAMP (cyclic adenosine-3',5'-monophosphate) hydrolytic inactivation. cAMP has been shown to be the second messenger mediating the biologic response to many of hormones, neurotransmitters and drugs (*Krebs Endocrinology Proceedings of the 4th International Congress Excerpta Medica,* 17–29, 1973). When the suitable agonist binds to the cell surface, the adenylated cyclase activates and turns $Mg^{2+}$-ATP into cAMP. cAMP modulates the activity of the majority, if not of all the cells contributing to the pathophysiology of various respiratory diseases, both of allergic origin and not. It follows that an increase of the cAMP concentration yields beneficial effects such as airway smooth muscle relaxation, inhibition of the mast cell mediator release (basophil granulose cells), suppression of the neutrophil and basophil degranulation, inhibition of the monocyte and macrophage activation. Thus, compounds able of activating adenylate cyclase or of inhibiting phosphodiesterases could suppress the undesired activation of the airway smooth muscle and of a great number of inflammatory cells.

In the phosphodiesterase family there is a distinct group of isoenzymes, phosphodiesterases 4 (hereinafter PDE 4) specific for the hydrolysis cAMP in the airway smooth muscle and inflammatory cells (Torphy, "*Phosphodiesterase Isoenzymes: Potential Targets for Novel Anti-asthmatic Agents*" in New Drugs for Asthma, Barnes, ed. IBC Technical Services Ltd, 1989). Studies carried out on this enzyme show that its inhibition yields not only the airway smooth muscle relaxation, but also the suppression of mastocyte, basophil and neutrophil degranulation, so as the inhibition of the monocyte and neutrophil activation. In addition, the action of PDE 4 inhibitors is markedly strengthened when the adenylate cyclase activity of the target cells is increased by endogenous hormones, as it happens in vivo. Thus PDE 4 inhibitors are effective in the therapy of asthma. Such compounds offer a unique approach to the therapy of various respiratory diseases, both of allergic origin and not, and possess significant therapeutic advantages over the current therapy.

The excessive or irregular production of tumour necrosis factor (hereinafter $TNF_\alpha$), a cytokine with pro-inflammatory activity produced by various kinds of cells, affects the mediation or the exacerbation of many pathologies such as, for example, the adult respiratory distress syndrome (ARDS) and the chronic pulmonary inflammatory disease. Therefore compounds able to control the negative effects of $TNF_\alpha$, i.e. the inhibitors of this cytokine, are to be considered as useful against many pathologies.

The patent application EP 0 490 823 (Sandoz) illustrates isoquinolines of formula

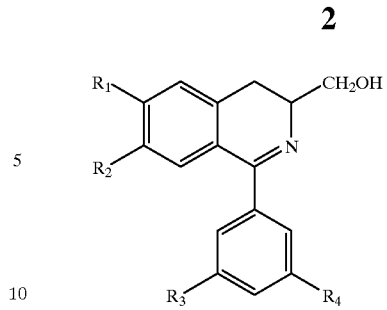

wherein
$R_1$–$R_4$ are lower alkoxy groups, as inhibitors of phosphodiesterase III, IV and V.

The patent application EP 0 491 441 (Shell Internationale Research) describes, inter alia, isoquinolines of formula

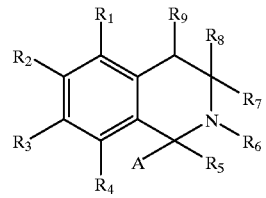

wherein $R_1$–$R_4$ are hydrogen, alkyl or alkoxy; $R_5$ and $R_6$ are hydrogen or together form a bond; $R_7$ is hydrogen, alkyl or alkoxy; $R_8$ and $R_9$ are hydrogen or together form a bond; and A is an optionally substituted phenyl. These compounds have fungicide activity in agricultural field.

The patent GB 1,199,768 (Pfizer) describes, inter alia, compounds of formula

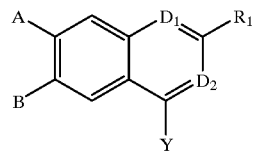

wherein A and B are independently hydrogen or ($C_{1-5}$) alkoxy; $R_1$ is hydrogen, an optionally substituted alkyl, benzyl, phenyl or phenethyl group, $D_1$ and $D_2$ are alternatively —N= or —CH=; and Y is —$NR_6R_7$ wherein $R_6$ and $R_7$ are independently hydrogen or an aryl up to 10 carbon atoms optionally substituted by 1–3 halogen atoms. These compounds are bronchodilators and anti-hypertensives.

The U.S. Pat. No. 5,556,862 (Nippon Zoki Pharmaceutical) claims pharmaceutical compositions containing isoquinolines of formula

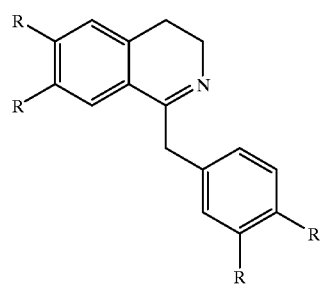

wherein R is hydrogen or alkoxy, useful as PDE 4 inhibitors.

The patent application WO 97/04779 (Chirosciente) claims, inter alia, quinolinones of formula

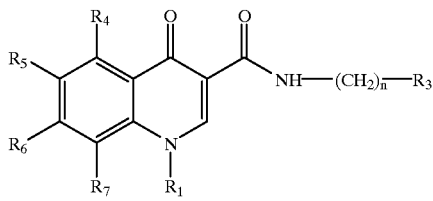

wherein $R_1$ is $(C_{1-6})$alkyl or $(C_{1-6})$alkyl-heterocycle optionally substituted by halogen atoms; $R_3$ is phenyl or pyridyl, furyl, etc.: $R_4$–$R_7$ are hydrogen or $(C_{1-6})$alkoxy, and n is 0–3. These compounds are PDE 4 and $TNF_\alpha$ inhibitors.

The patent application EP 0 569 592 (Otsuka) describes quinolinones of formula

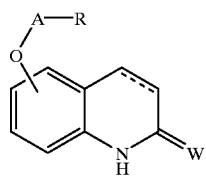

wherein R represents several kinds of chains ending with an amino group; A is lower alkylene and W is O or S. These compounds are phosphodiesterase inhibitors in general with particular reference to an inhibiting activity of piastrinic aggregation.

The patent application WO 97/38977 (Astra) claims isoquinolines of formula

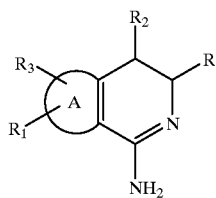

wherein R can be alkyl or a cyclic substituent, $R_1$ can be hydrogen or phenylalkyl, $R_2$ can be hydrogen, alkyl or phenyl-alkynyl and $R_3$ is hydrogen or a halogen atom. These compounds have anti-inflammatory activity.

The patent application EP 0 848 000 (Tanabe Seiyaku) describes compounds of formula

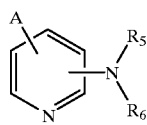

wherein A is one of the rings

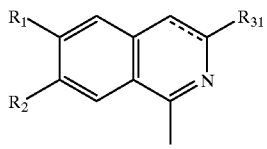

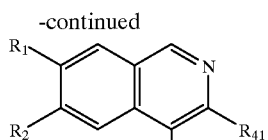

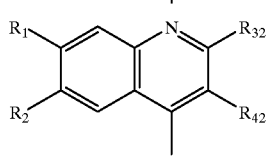

wherein $R_1$ and $R_2$ are hydrogen or an optionally protected hydroxy group; $R_{31}$, $R_{41}$, and $R_{42}$ are optionally protected hydroxymethyl; $R_{32}$ is hydrogen, lower alkyl or optionally protected hydroxymethyl; and $R_5$ and $R_6$ are hydrogen, amino or can form a heterocycle. These compounds are PDE 4 inhibitors.

It has been now surprisingly found a new class of benzazine derivatives able to selectively inhibit PDE 4 and further to inhibit $TNF_\alpha$.

DETAILED DESCRIPTION OF THE INVENTION

Therefore the present invention relates to compounds of formula

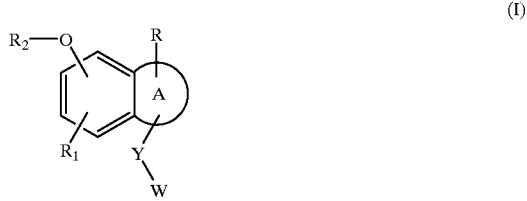

(I)

wherein

A is a heterocycle containing a nitrogen atom and optionally unsaturated and optionally further substituted by an oxo group (=O);

R is hydrogen, cyano, $(C_{1-4})$alkoxycarbonyl, carbamoyl; optionally substituted $(C_{4-7})$-cycloalkyl, aryl or heterocycle; $(C_{1-8})$alkyl, $(C_{2-8})$alkenyl or $(C_{2-8})$alkynyl optionally branched and/or substituted by $(C_{4-7})$ cycloalkyl, aryl or heterocycle; aryloxy, heterocyclyloxy, aryl-$(C_{1-4})$alkoxy, heterocyclyl$(C_{1-4})$ alkoxy, amino substituted by one or two $(C_{1-4})$alkyl group(s), aryl-amino, heterocyclyl-amino, aryl$(C_{1-4})$ alkyl-amino heterocyclyl$(C_{1-4})$alkylamino;

Y is methylene or ethylene;

W is an optionally substituted aryl or heterocycle:

$R_1$ is hydrogen, $(C_{4-7})$cycloalkyl or a $(C_{1-8})$alkyl, $(C_{2-8})$ alkenyl or $(C_{2-8})$alkynyl group optionally substituted by hydroxy, oxo, $(C_{4-7})$cycloalkyl, aryl or heterocycle, and optionally interrupted by one or more heteroatom(s) or heterogroup(s);

$R_2$ is a $(C_{1-6})$alkyl or polyfluoro$(C_{1-6})$alkyl group;

the N→O derivatives of the compounds of formula I and the pharmaceutically acceptable salts thereof.

The compounds of formula I can have an asymmetric centre and thus be in form of stereoisomers. Object of the present invention are compounds of formula I in form of stereoisomeric mixtures so as of single stereoisomers.

Preferred compounds according to the invention are those of formula I wherein R is hydrogen, $(C_{4-7})$cycloalkyl, aryl, ($C_{1-8}$)alkyl optionally branched and/or substituted by ($C_{4-7}$)-cycloalkyl or aryl; $R_1$ is hydrogen, ($C_{4-7}$)cycloalkyl or a ($C_{1-8}$)alkyl optionally substituted by ($C_{4-7}$)cycloalkyl, aryl or heterocycle, and optionally interrupted by one or more heteroatoms or heterogroups; and W is an optionally substituted heterocycle.

Still more preferred compounds according to the invention are those of formula I wherein R is hydrogen, ($C_{4-7}$) cycloalkyl, aryl, ($C_{1-8}$)alkyl optionally branched and/or substituted by ($C_{4-7}$)cycloalkyl or aryl; $R_1$ is hydrogen and W is a substituted pyridine.

The compounds of formula I are active as selective PDE 4 and $TNF_\alpha$ inhibitors and thus are used as therapeutic agents in allergic and inflammatory pathologies such as, for example, emphysema, chronic bronchitis, asthma and allergic rhinitis.

As heterocycle it is meant an optionally partially or totally hydrogenated aromatic ring containing one or more heteroatom(s) selected among oxygen, nitrogen and sulfur, for example pyrrole, imidazole, pyrazole, pyridine, pyrazine, pyrimidine, pyridazine, piperazine, triazine, morpholine, pyrrolidine, pyrroline, imidazoline, pyrazoline, pyrazolidine, imidazolidine, piperidine, furan, pyran, isothiazole, isoxazole, thiophene and the like.

Specific example of alkyl groups are methyl, ethyl, n-propyl, i-propyl, n-butyl, s-butyl, t-butyl, n-pentyl, 1-methyl-butyl, 2-ethyl-propyl, 3-methyl-butyl, 3-methyl-2-butyl, n-hexyl, heptyl, octyl and the like. As ($C_{4-7}$)cycloalkyl group cyclobutyl, cyclopentyl, cyclohexyl and cycloheptyl are meant, and when it contains an oxygen atom, tetrahydrofuran or tetrahydropyran, for example, are meant, while aryl means an aromatic $C_{6-10}$ ring or system such as, for example, phenyl, naphthyl, indanyl, and the like.

Specific examples of substituents present on the W ring are halogens, such as chlorine, bromine, fluorine and iodine, ($C_{1-4}$)alkyl, hydroxy, nitro and carboxy.

The N→O group optionally present in the compounds of formula I can be both on the nitrogen of the benzazine ring and on those optionally present on the W substituent.

Pharmaceutically acceptable salts of the compounds of formula I are those with organic and inorganic acids, such as, for example, hydrochloric, hydrobromic, hydroiodic, nitric, sulfuric, phosphoric, acetic, benzoic, maleic, fumaric, succinic, tartaric, citric, aspartic, methanesulfonic and 3,7-di-t.butylnaphthalen-1,5-disulfonic (dibudinic acid).

The preparation of the compounds of formula I proceeds according to methods for the synthesis of benzazine derivatives known to the skilled in the art (see, for example Chemistry of Heterocyclic Compounds, NY, London). Herein after the synthesis of some compounds of formula I is illustrated in more details while for others reference is made to the specific examples.

For example, when compounds of formula I being 3,4-dihydro-isoquinolines are to be obtained, the synthesis starts from a compound of formula

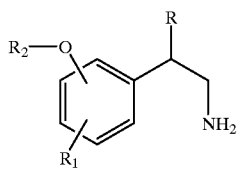

(II)

wherein R, $R_1$, $R_2$ are as defined above, which is reacted with a compound of formula

W—Y—Z (III)

wherein W and Y are as defined above, and Z is a carboxy group or a reactive derivative thereof such as, for example, the acyl chloride. When Z is a carboxy group the reaction occurs in the presence of activating agents such as, for example, 1-hydroxybenzotriazole (HOBT), dicyclohexylcarbodiimide (DCC) or carbonyldiimidazole. Thus it is obtained a compound of formula

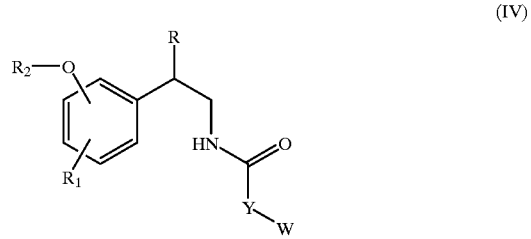

(IV)

wherein $R_1$, $R_2$, R, W and Y are as defined above, which is cyclised, for example, in the presence of phosphoryl chloride. The result of this cyclisation depends on the position of $R_1$ and —$OR_2$ and can bring to one or more isomer(s) which are separated, for example, by chromatographic techniques or by crystallisation.

The intermediate of formula II can be obtained starting from an aldehyde of formula

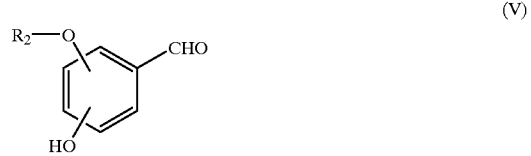

(V)

wherein $R_2$ is as defined above, whose hydroxy function is activated, for example with triflic anhydride, to give a compound of formula

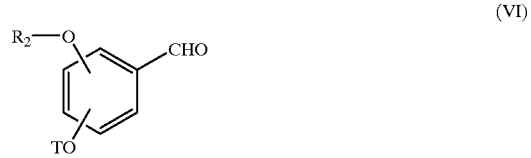

(VI)

wherein $R_2$ is as defined above, and T is an activating group. This compound undergoes a coupling reaction in the presence of a catalyst, for example palladium, to give an aldheyde of formula

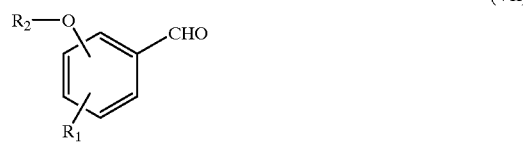

(VII)

wherein $R_1$ and $R_2$ are as defined above. This is reacted with nitromethane to give a compound of formula

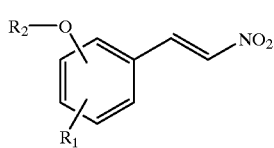

(VIII)

wherein R₁ and R₂ are as defined above, which is reduced, for example with lithium aluminium hydride, to give the intermediate of formula II (R=H).

The compound of formula II (R≠H) is obtained by reacting the compound VIII with the suitable metalloorganic for example a Grignard reactive, to give a compound of formula

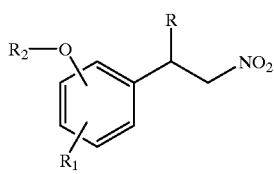

(IX)

wherein R₁ and R₂ are as defined above and R is different from H, which by reduction, for example with Pd/C, gives the corresponding intermediate of formula II.

Alternatively, the intermediate II (R≠H) is prepared starting from a compound of formula

R—X (X)

wherein R is different from H and X is a chlorine, bromine or iodine atom, or a hydroxy group. When X is hydroxy, this is activated with a suitable activating agent, for example p-toluensulphonyl, according to conventional methods. This compound is reacted with a compound of formula

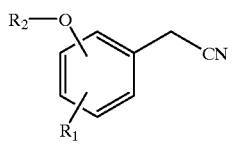

(XI)

wherein R₁ and R₂ are as defined above, in the presence of a base such as, for example, sodium hydride, to give a compound of formula

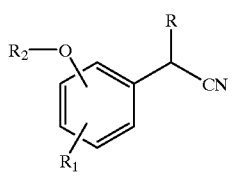

(XII)

wherein R₁ and R₂ are as defined above and R is different from H, which is reduced, for example with lithium aluminium hydride, to give the compound of formula II (R≠H). Another example of synthesis relates to the compounds of formula I wherein A is a heterocycle substituted by —Y—W on the nitrogen atom and further substituted by an oxo group. In this case the preparation starts from the compounds of formula

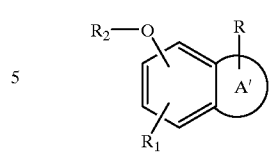

(XIII)

wherein R, R₁ and R₂ are as defined above and A' is a heterocycle containing a nitrogen atom, optionally unsaturated and substituted by an oxo group in a suitable position. These compounds are known in the literature or can be easily prepared by the skilled in the art. The compound XIII is treated with a compound of formula

W—Y—X (XIV)

wherein W, Y and X are as defined above in the presence of sodium hydride to give the desired compound of formula I.

The synthesis of the N-oxides of the compounds of formula I occurs by treating the compounds of formula I with peracids such as, for example, m-chloroperbenzoic acid.

The preparation of the salts of the compounds I is effected according to conventional methods.

The compounds of formula I are selective PDE 4 inhibitors as showed by the inhibition tests on the isolated enzyme (example 55).

It is apparent how these enzymatic selectivity and specificity features combined with the lack of activity on the cardiovascular system make the compounds of formula I specifically suitable for treating pathologies involving PDE 4 and TNFα even if in the present contest the interest is particularly focused on the respiratory pathologies. In particular the compounds of the invention are useful for treating allergic and inflammatory diseases and above all for treating emphysema, chronic obstructive pulmonary disease (COPD) and chronic bronchitis specifically, asthma and allergic rhinithis.

The therapeutic doses shall be generally from 0.1 to 1,000 mg a day and from 1 to 100 mg by oral route for single administration.

A further object of the present invention are the pharmaceutical compositions containing a therapeutically effective amount of the compounds of formula I or pharmaceutically acceptable salts thereof in admixture with a suitable carrier.

The pharmaceutical compositions object of the invention can be liquid, suitable for the enteral or parenteral administration, and, preferably, solid such as tablets, capsules. granulates, suitable for the oral administration, or in a form suitable for the transdermal and inhalatory administration.

The preparation of the pharmaceutical compositions object of the invention can be effected according to common techniques.

For better illustrating the invention the following examples are now provided.

The ¹H-NMR spectra were run at 200 MHz on a Varian instrument: δ are in parts per million.

EXAMPLE 1

Toluen-4-sulphonic acid 5-phenyl-pentyl ester

To a solution of 5-phenyl-1-pentanol (3.28 g, 20 mmoles) and triethylamine (6.13 ml, 44 mmoles) in CH₂Cl₂ (35 ml) under N₂, p-toluen-sulphonyl chloride (4.19 g, 22 mmoles)

was added and then put under stirring up to room temperature for 1 night. The mixture was washed with water, NaHCO₃ and 5% HCl, anhydrified and brought to dryness to give 6.55 g of the title compound (yield: 100%).

¹H-NMR (CDCl₃): 7.79–7.10(m,9H); 4.00(t,2H,JHH=6.4 Hz); 2.58–2.51(m,2H); 2.43(s,3H); 1.72–1.28(m,6H).

EXAMPLE 2

2-(3-Methoxy-phenyl)-7-phenyl-heptan-nitrile

NaH (55–65%, 880 mg, 22 mmoles) was added to a solution of 3-methoxy-phenyl-acetonitrile (2.94 g, 20 mmoles) in DMF (25 ml) under N₂ and the mixture was kept under stirring for 30 minutes, then toluen-4-sulphonic acid 5-phenyl-pentyl ester (6.37 mg, 20 mmoles), obtained as described in example 1, was added and the stirring was kept on for 1 hour. The mixture was poured into water and extracted with ethyl ether. The organic phase was brought to dryness and the residue purified by chromatography (eluent: petrolatum/ethyl ether 95:5) to give 3.3 g of the title compound (yield: 56.2%).

¹H-NMR (CDCl₃): 7.31–6.81(m,9H); 3.80(s,3H); 3.75–3.67(m,1H); 2.62–2.55(m,2H); 1.94–1.30(m,8H).

EXAMPLE 3

2-(3-Methoxy-phenyl)-7-phenyl-heptylamine

A solution of 2-(3-methoxy-phenyl)-7-phenyl-heptan-nitrile (3.3 g, 11.25 mmoles), obtained as described in example 2, in ethyl ether (30 ml) was added dropwise to a suspension of LiAlH₄ (427 mg, 11.25 mmoles) in anhydrous ethyl ether (30 ml) under N₂ at room temperature. The mixture was kept under stirring at room temperature for 1 hour. The hydride was decomposed with water (0.5 ml), 10% NaOH (0.75 ml) and water (1.25 ml). The mixture was filtered, washed with warm ethyl ether anhydrified and brought to dryness to give 3.22 g of the title compound (yield: 96.2%).

¹H-NMR (CDCl₃): 7.29–6.69(m,9H); 3.79(s,3H); 2.94–2.46(m,5H); 1.70–1.11(m,10H).

EXAMPLE 4

2-(3,5-Dichloro-pyridin-4-yl)-N-[2-(3-methoxy-phenyl)-7-phenyl-heptyl]-acetamide A solution of (3,5-dichloro-pyridin-4-yl)-acetic acid (2.06 g, 10 mmoles) and carbonyldiimidazole (1.78 g, 11 mmoles) in THF (30 ml) was kept under stirring for 1 hour under N₂. 2-(3-Methoxy-phenyl)-7-phenyl-heptylamine (2.97 g, 10 mmoles), obtained as described in example 3, was added and the stirring was kept on for 1 hour, then the mixture was brought to dryness, the residue taken up with ethyl acetate and extracted with KHSO₄, NaHCO₃ and anhydrified. After evaporation to dryness an oil which was adsorbed on SiO₂ was obtained and percolated with ethyl acetate/petrolatum 1:3 to give 4.57 g of the title compound (yield: 97.6%).

¹H-NMR (CDCl₃): 8.40(s,2H); 7.28–6.60(m,9H); 5.20 (bt,1H); 3.78(s,3H); 3.75(s,2H); 3.73–3.04(m,2H); 2.74–2.59(m,1H); 2.55–2.48(m,2H); 1.61–1.14(m,8H).

EXAMPLE 5

1-(3,5-Dichloro-pyridin-4-ylmethyl)-6-methoxy-4-(5-phenyl-pentyl)-3,4-dihydro-isoquinoline dihydrochloride and 1-(3,5-dichloro-pyridin-4-ylmethyl)-8-methoxy-4-(5-phenyl-pentyl)-3,4-dihydro-isoquinoline dihydrochloride (Compounds 1 and 2)

A solution of 2-(3,5-dichloro-pyridin-4-yl)-N-[2-(3-methoxy-phenyl)-7-phenyl-heptyl]-acetamide (4.5 g, 9.27 mmoles), obtained as described in example 4, POCl₃ (3.39 ml, 37.08 mmoles) in CH₃CN (45 ml) was kept under reflux for 2 hours under N₂, then brought to dryness and the residue taken up with water, neutralised with NaHCO₃ and extracted with CH₂Cl₂. The organic phase was washed, anhydrified and brought to dryness to give an oil which was chromatographed to give two separated products which were salified with HCl/ethyl ether to give 2.6 g of Compound 1 (yield: 51.9%) and 0.45 g of Compound 2 yield: 8.98%).

a) Compound 1: ¹H-NMR (DMSO): 8.71(s,2H); 8.10–7.10(m,7H); 5.10–4.82(m,2H); 3.92(s,3H); 3.79–3.73 (m,2H); 3.13–3.02(m,1H); 2.56–2.48(m, 2H); 1.60–1.19(m, 10H).

b) Compound 2: ¹H-NMR (DMSO): 8.69(s,2H); 7.81–7.04(m,8H); AB system: Va=5.00, Vb=4.75, JAB=18.8 Hz: 3.90(s,3H); 373–3.66(m,2H); 3.08–2.98(m,1H); 2.53(t, 2H); 1.59–1.18(m,8H).

EXAMPLE 6

Toluen-4-sulphonic acid cyclopentylmethyl ester

A solution of cyclopentan-methanol (2 g, 20 mmoles), CH₂Cl₂ (20 ml), triethylamine (5.85 ml, 42 mmoles) and p-toluen-sulphonyl chloride (4 g, 21 mmoles) was kept under stirring at room temperature for 1 night, then washed with water, 5% HCl and NaHCO₃ and evaporated to give 5.09 g of the title compound (yield: 100%).

¹H-NMR (CDCl₃): 7.79–7.30(m,4H); 3.87(d, 1H,JHH= 7.2 Hz); 2.43(s,3H); 2.29–1.06(m,9H).

EXAMPLE 7

3-Cyclopentyl-2-(3-methoxy-phenyl)-propionitrile

By working in a way similar to that described in example 2 but using toluen-4-sulphonic acid cyclopentylmethyl ester (5.09 g, 20 mmoles), obtained as described in example 6, 3-methoxy-phenyl-acetonitrile (2.94 g, 20 mmoles), NaH (55–65%, 880 mg, 22 mmoles) and DMF (25 ml), 2.3 g of the title compound were obtained (yield: 50.1%).

¹H-NMR (CDCl₃): 7.31–6.80(m,4H); 3.80(s,3H); 3.75–3.67(m,1H); 2.09–1.04(m,11H).

EXAMPLE 8

3-Cyclopentyl-2-(3-methoxy-phenyl)-propylamine

A solution of 3-cyclopentyl-2-(3-methoxy-phenyl)-propionitrile (2.3 g, 10 mmoles), obtained as described in example 7, in ethyl ether (25 ml) was added to a suspension of LiAlH₄ (380 mg, 10 mmoles) in ethyl ether (30 ml), under N₂, and the mixture was kept under stirring at room temperature for 1 hour. The hydride was decomposed with water (0.4 ml), 10% NaOH (0.5 ml) and water again (1 ml). The mixture was filtered, washed with ethyl ether and water. The organic phase was evaporated to give 2.2 g of the title compound (yield: 94.3%).

¹H-NMR (CDCl₃): 7.25–6.72(m,4H); 3.78(s,3H); 2.92–2.52(m,3H); 1.76–0.95(m,11H).

EXAMPLE 9

N-[3-cyclopentyl-2-(3-methoxy-phenyl]-2-(3,5-dichloro-pyridin-4-yl)-acetamide

By working in a way similar to that described in example 4 but using (3,5-dichloro-pyridin-4-yl)-acetic acid (1.94 g, 9.43 mmoles), carbonyldiimidazole (1.68 g, 10.373 mmoles), THF (30 ml) and 3-cyclopentyl-2-(3-methoxy-phenyl)-propylamine (2.2 g, 9.43 mmoles), obtained as described in example 8, 3.35 g of the title compound were obtained (yield: 98.3%), m.p.: 106–107° C.

$^1$H-NMR (CDCl$_3$): 8.41(s,2H); 7.21–6.62(m,4H); 5.15 (bs,1H); 3.78(s,3H); 3.75(s,2H); 3.74–3.02(m,2H); 2.79–2.65(m,1H); 2.56–2.49(m,2H); 1.74–0.94(m,11H).

EXAMPLE 10

4-Cyclopentylmethyl-1-(3,5-dichloro-pyridin-4-ylmethyl)-6-methoxy-3,4-dihydro-isoquinoline dihydrochloride and 4-cyclopentylmethyl-1-(3,5-dichloro-pyridin-4-ylmethyl)-8-methoxy-3,4-dihydro-isoquinoline dihydrochloride (Compounds 3 and 4)

By working in a way similar to that described in example 5 but using N-[3-cyclo-pentyl-2-(3-methoxy-phenyl)-propyl]-2-(3,5-dichloro-pyridin-4-yl)-acetamide (3.2 g, 7.6 mmoles), obtained as described in example 9, POCl$_3$ (2.78 ml, 30.4 mmoles) and CH$_3$CN (35 ml), 1 g of Compound 3 (yield: 27.6%) and 0.37 g of Compound 4 (yield: 10.2%) were obtained.

a) Compound 3—m.p.: 162–164° C. (dec.)

$^1$H-NMR (DMSO): 8.71(s,2H); 8.58(bs,2H); 8.06(d,1H, JHH=8.4Hz); 7.14–7.07(m,2H); AB system: VA=5.06, VB=4.88, JAB=18.3 Hz; 3.91(s,3H); 3.81–3.73(m,2H); 3.14–3.03(m,1H); 1.86–1.00(m,11H).

b) Compound 4—m.p.: 189–190° C. (dec.)

$^1$H-NMR (DMSO): 8.71(s,2H); 7.82–7.20(m,3H); AB system: VA=5.02, VB=4.78, JAB=18.9 Hz; 3.89(s,3H); 3.76–3.69(m,2H); 3.12–3.01(m,1H); 1.86–1.00(m,11H).

EXAMPLE 11

Toluen-4-sulphonic acid 6-phenyl-hexyl ester

A solution of 6-phenyl-1-hexanol (2.9 g, 16.27 mmoles), CH$_2$Cl$_2$ (30 ml), triethylamine (4.76 ml, 34.16 mmoles) and p-toluensulphonyl chloride (3.26 g, 17.08 mmoles) was kept under stirring at room temperature for 1 night, washed with water, 5% HCl and NaHCO$_3$ and evaporated to give 5.4 g of the title compound (yield: 100%).

$^1$H-NMR (CDCl$_3$): 7.80–7.11(m,9H); 4.00(t,2H,JHH=6.4 Hz) 2.59–2.51(m,2H); 2.42(s,3H); 1.68–1.21(m,8H).

EXAMPLE 12

2-(3-Methoxy-phenyl)-8-phenyl-octan-nitrile

By working in a way similar to that described in example 2 but using toluen-4-sulphonic acid 6-phenyl-hexyl ester (5.4 g, 16.24 mmoles), obtained as described in example 11, 3-methoxy-phenyl-acetonitrile (2.39 g, 16.24 mmoles), NaH (55–65%, 715 mg, 17.86 mmoles) and DMF (25 ml), 2.7 g of the title compound were obtained (yield: 54.1%).

$^1$H-NMR (CDCl$_3$): 7.32–6.82(m,9H); 3.81(s,3H); 3.76–3.68(m,1H); 2.62–2.55(m,2H); 1.94–1.30(m,10H).

EXAMPLE 13

2-(3-Methoxy-phenyl)-8-phenyl-octylamine

A solution of 2-(3-methoxy-phenyl)-8-phenyl-octan-nitrile (2.7 g, 8.78 mmoles), obtained as described in example 12, in ethyl ether (30 ml) was added to a suspension of LiAlH$_4$ (333 mg, 8.78 mmoles) in ethyl ether (30 ml), under N$_2$, and the mixture was kept under stirring at room temperature for 1 hour. The hydride was decomposed with water (0.4 ml), 10% NaOH (0.5 ml) and water again (1 ml). The mixture was filtered, washed with ethyl ether and water. The organic phase was evaporated to give 2.5 g of the title compound (yield: 91.4%).

$^1$H-NMR (CDCl$_3$): 7.29–6.70(m,9H); 3.79(s,3H); 2.93–2.45(m,5H); 1.65–1.13(m,10H).

EXAMPLE 14

2-(3,5-Dichloro-pyridin-4-yl)-N-[2-(3-methoxy-phenyl)-8phenyl-octyl]-acetamide

By working in a way similar to that described in example 4 but using (3,5-dichloro-pyridin-4-yl)-acetic acid (1.65 g, 8.026 mmoles), carbonyldiimidazole (1.43 g, 8.829 mmoles), THF (25 ml) and 2-(3-methoxy-phenyl)-8-phenyl-octylamine (2.5 g, 8.026 mmoles), obtained as described in example 13, 3.39 g of the title compound were obtained (yield: 84.6%), m.p.: 97–98° C.

$^1$H-NMR (CDCl$_3$): 8.41(s,2H); 7.28–6.61(m,9H); 5.16 (bt,1H); 3.78(s,3H); 3.75(s,2H); 3.74–3.03(m,2H); 2.74–2.59(m,1H); 2.56–2.49(m,2H); 1.60–1.11(m,10H).

EXAMPLE 15

1-(3,5-Dichloro-pyridin-4-ylmethyl)-6-methoxy-4-(6-phenyl-hexyl)-3,4-dihydro-isoquinoline dihydrochloride and 1-(3,5-dichloro-pyridin-4-ylmethyl)-8-methoxy-4-(6-phenyl-hexyl)-3,4-dihydro-isoquinoline dihydrochloride (Compounds 5 and 6)

By working in a way similar to that described in example 5 but using 2-(3,5-dichloropyridin-4-yl)-N-[2-(3-methoxy-phenyl)-8-phenyl-octyl]-acetamide (3.25 g, 6.51 mmoles), obtained as described in example 14, POCl$_3$ (2.38 ml, 26.04 mmoles) and CH$_3$CN (35 ml), 2.32 g of Compound 5 (yield: 64.3%) and 0.3 g of Compound 6 (yield: 10.2%) were obtained.

a) Compound 5—m.p.: 135–137° C. (dec.)

$^1$H-NMR (DMSO): 8.72(s,2H); 8.11–7.09(m,8H); 7.77 (bs, 2H); AB system: Va=5.05, Vb=4.87, JAB=18.5 Hz; 3.91(s,3H); 3.76(bs,2H); 3.12–3.03(m,1H); 2.53(t,2H); 1.59–1.18(m,10H).

b) Compound 6—m.p.: 117–119° C. (dec.)

$^1$H-NMR (DMSO): 8.69(s,2H); 7.80–7.03(m,8H); AB system: Va=5.00, Vb=4.74, JAB=18.8 Hz); 3.89(s,3H); 3.69 (broad signal,2H); 3.08–2.97(m,1H); 2.54(t,2H); 1.59–1.18 (m,10H).

EXAMPLE 16

2-(3-Methoxy-phenyl)-pentan-nitrile

NaH (55–65%, 1.44 g, 36 mmoles) and, after 30 minutes under stirring, 1-bromo-propane (4.46 g, 36 mmoles) were added to a solution of 3-methoxy-phenyl-acetonitrile (4.4 g, 30 mmoles) in anhydrous DMF (30 ml) under N$_2$ at room temperature. After 1.5 hours the mixture was poured into water (200 ml), extracted 3 times with ethyl ether, anhydrified and brought to dryness to give a residue which was chromatographed (eluent: petrolatum, then petrolatum/ethyl ether 95:5) to give 4.2 g of the title compound (yield: 74%).

$^1$H-NMR (CDCl$_3$): 7.81–7.31(m,4H); 3.80(s,3H); 3.77–3.70(m,1H); 2.00–1.38(m,2H); 0.94(t,3H,JHH=7.4 Hz).

EXAMPLE 17

2-(3-Methoxy-phenyl)-pentylamine

A solution of 2-(3-methoxyphenyl)-pentan-nitrile (4.2 g, 0.022 moles), obtained as described in example 16, in anhydrous ethyl ether (25 ml) was added dropwise to a suspension of LiAlH$_4$ (0.84 g, 0.022 moles) in anhydrous ethyl ether (40 ml) under N$_2$ at room temperature. After 2 hours water (0.84 ml), 10% NaOH (1.6 ml) and water (0.84 ml) were added, it was filtered and washed with ethyl ether. The organic phase was extracted with 10% HCl. The aqueous acid phase was basified with K$_2$CO$_3$, extracted with ethyl ether which was anhydrified and brought to dryness to give 3.9 g of the title compound (yield: 90.9%).

$^1$H-NMR (CDCl$_3$): 7.25–6.70(m,4H); 3.78(s,3H); 2.94–2.53(m,5H); 2.16(bs,2H); 1.63– 1.10(m,2H); 0.84(t, 3H,JHH=7.4 Hz).

EXAMPLE 18

2-(3,5-Dichloro-pyridin-4-yl)-N-[2-(3-methoxy-phenyl)-pentyl]-acetamide

By working in a way similar to that described in example 4 but using (3,5-dichloro-pyridin-4-yl)-acetic acid (2.06 g, 10 mmoles), carbonyldiimidazole (1.78 g, 11 mmoles), THF (30 ml) and 2-(3-methoxy-phenyl)-pentylamine (1.93 g 10 mmoles), obtained as described in example 17, 3.7 g of the title compound were obtained (yield: 97%), m.p.: 97–98° C.

$^1$H-NMR (CDCl$_3$): 8.41(s,2H); 7.20–6.61(m,4H); 5.19 (bt,1H); 3.78(s,3H); 3.75(s,2H); 3.75–3.03(m,2H); 2.77–2.62(m,1H); 1.60–1.08 (m,4H); 0.82(t,3H,JHH=7.4 Hz).

EXAMPLE 19

1-(3,5-Dichloro-pyridin-4-ylmethyl)-6-methoxy-4-propyl-3,4-dihydro-isoquinoline dihydrochloride and 1-(3,5-dichloro-pyridin-4-ylmethyl)-8-methoxy-4-propyl-3,4-dihydro-isoquinoline dihydrochloride (Compounds 7 and 8)

By working in a way similar to that described in example 5 but using 2-(3,5-dichloro-pyridin-4-yl)-N-[2-(3-methoxy-phenyl)-pentyl]-acetamide (3.4 g, 8.92 mmoles), obtained as described in example 18, POCl$_3$ (3.26 ml, 35.66 mmoles) and CH$_{3CN}$ (35 ml), 1.62 g of Compound 7 (yield: 41.6%) and 0.44 g of Compound 8 (yield: 11.3%) were obtained.

a) Compound 7—$^1$H-NMR (DMSO): 8.73(s,2H); 8.12–7.10 (m,3H); AB system: Va=5.06, Vb=4.88, Jab=18.5 Hz; 3.93(s,3H); 3.80–3.73(m,2H); 3.19–3.04(m,1H); 1.55–1.13(m,4H); 0.87(t,3H,JHH=7.1 Hz).

b) Compound 8—$^1$H-NMR (DMSO): 8.70(s,2H); 7.83–7.06 (m,3H); AB system: Va=5.03, Vb=4.81, Jab=18.9 Hz; 3.87(s,3H); 3.76–3.70 (m,2H) 3.15–3.04(m,1H); 1.59–1.13(m,4H); 0.91–0.83(m,3H).

EXAMPLE 20

2-(3-Methoxy-phenyl)-4-methyl-pentan-nitrile

By working in a way similar to that described in example 16 but using 3-methoxy-phenyl-acetonitrile (4.4 g, 30 mmoles), anhydrous DMF (30 ml), NaH (55–65%, 1.44 g, 36 mmoles) and isobutylbromide (4.97 g, 36 mmoles), 3.8 g of the title compound were obtained (yield: 62.3%).

EXAMPLE 21

2-(3-Methoxy-phenyl)-4-methyl-pentylamine

By working in a way similar to that described in example 17 but using LiAlH$_4$ (0.7 g, 0.018 moles) in anhydrous ethyl ether (35 ml) and 2-(3-methoxy-phenyl)-4-methyl-pentan-nitrile (3.8 g, 0.018 moles), obtained as described in example 20, in anhydrous ethyl ether (35 ml), 3.5 g of the title compound were obtained (yield: 90.4%).

$^1$H-NMR (CDCl$_3$): 7.25–6.71(m,4H); 3.78(s,3H); 2.89–2.57(m,3H); 1.61–1.33(m,5H); 0.82(m,6H).

EXAMPLE 22

2-(3,5-Dichloro-pyridin-4-yl)-N-[2-(3-methoxy-phenyl)-4-methyl-pentyl]-acetamide By working in a way similar to that described in example 4 but using (3,5-dichloropyridin-4-yl)-acetic acid (2.06 g, 10 mmoles), carbonyldiimidazole (1.78 g, 11 mmoles), THF (30 ml) and 2-(3-methoxy-phenyl)-4-methyl-pentylamine (2.07 g, 10 mmoles), obtained as described in example 21, 3.85 g of the title compound were obtained (yield: 97.6%), m.p.: 98–99° C.

$^1$H-NMR (CDCl$_3$): 8.41(s,2H); 7.21–6.62(m,4H); 5.20 (bt,1H); 3.78(s,3H); 3.75(s,2H); 43.7–3.00(m,2H); 2.85–2.71(m,1H); 1.59–1.30(m,3H); 0.83–0.79(m,6H).

EXAMPLE 23

1-(3,5-Dichloro-pyridin-4-ylmethyl)-4-isobutyl-6-methoxy-3,4-dihydro-isoquinoline dihydrochloride and 1-(3,5-dichloro-pyridin-4-ylmethyl)-4-isobutyl-8-methoxy-3,4-dihydro-isoquinoline dihydrochloride (Compounds 9 and 10)

By working in a way similar to that described in example 5 but using 2-(3,5-dichloro-pyridin-4-yl)-N-[2-(3-methoxy-phenyl)-4-methyl-pentyl]-acetamide (3.4 g, 8.6 mmoles), obtained as described in example 22, POCl$_3$ (3.15 ml, 34.4 mmoles) and CH$_3$CN (35 ml), 1.37 g of Compound 9 (yield: 35.4%) and 0.4 g of Compound 10 (yield: 10.3%).

a) Compound 9—$^1$H-NMR (DMSO): 12.45(bs,1H); 8.75(s, 2H); 8.15–7.07(m,3H); AB system: Va=5.05, Vb=4.89, Jab=18.5 Hz; 3.93(s,3H); 3.84–3.67(m,2H); 3.22–3.09(m, 1H); 1.62–1.28(m,3H); 0.94–0.86(m,6H).

b) Compound 10—$^1$H-NMR (DMSO): 8.72(s,2H); 7.82–7.05 (m,3H); AB system: Va=5.03, Vb=4.78, Jab= 18.9 Hz: 3.91(s,3H); 3.74–3.68 (m,2H); 3.20–3.07(m, 1H); 1.60– 1.43(m,1H); 1.39–1.30(m,2H) 0.94–0.85(m, 6H).

EXAMPLE 24

2-(3-Methoxy-phenyl)-butyronitrile

By working in a way similar to that described in example 16 but using 3-methoxy-phenyl-acetonitrile (8.8 g, 60 mmoles), DMF (60 ml), NaH (60%, 2.88 g, 72 mmoles) and ethylbromide (7.85 g, 72 mmoles), and chromatographing with petrolatum/ethyl ether 97:3 as eluent, 6.1 g of the title compound were obtained (yield: 58%).

$^1$H-NMR (CDCl$_3$): 7.31–6.81(m,4H); 3.80(s,3H); 3.60(t, 1H,JHH=7.2 Hz); 2.00–1.85(m,2H); 1.06(t,3H,JHH=7.4 Hz).

EXAMPLE 25

2-(3-Methoxy-phenyl)-butylamine

A solution of 2-(3-methoxy-phenyl)-butyronitrile (6.1 g, 35 mmoles), obtained as described in example 24, in ethyl ether (20 ml) was added dropwise to a suspension of LiAlH$_4$ (1.32 g, 35 mmoles) in ethyl ether (40 ml) under N$_2$ at room temperature. After 1 hour the hydride was decomposed with water (1.3 ml), 10% NaOH (2.6 ml) and water (1.3 ml). The mixture was filtered, washed with ethyl ether, dried and evaporated to give the title compound. The mother liquors were concentrated, added with triethanolamine (3 ml), kept under stirring for some hours, extracted more times with ethyl ether and the organic phase was evaporated. The residue was joined to the previous compound and the whole was chromatographed to give 4.8 g of the title compound (yield: 77%).

$^1$H-NMR (CDCl$_3$): 7.24–6.69(m,4H); 3.78(s,3H);, 2.94–2.73 (m,2H); 2.51–2.37(m,1H); 1.76–1.40(m,2H); 1.22(s,2H); 0.79(t,3H,JHH=7.4 Hz).

EXAMPLE 26

2-(3,5-Dichloro-pyridin-4-yl)-N-[2-(3-methoxy-phenyl)-butyl]-acetamide

By working in a way similar to that described in example 4 but using (3,5-dichloro-pyridin-4-yl)-acetic acid (2.06 g, 10 mmoles), carbonyldiimidazole (1.78 g, 11 mmoles), THF (30 ml) and 2-(3-methoxy-phenyl)-butylamine (1.79 g, 10 mmoles), obtained as described in example 25, 3.55 g of the title compound were obtained (yield: 96.7%). m.p.: 104–105° C.

$^1$H-NMR (CDCl$_3$): 8.41(s,2H); 7.21–6.60(m,4H); 5.21 (bs,1H); 3.78(s,3H); 3.75(s,2H);3.76– 3.06(m,2H); 2.67–2.52(m,1H); 1.72–1.44(m,2H); 0.74(t,3H,JHH=7.4 Hz).

EXAMPLE 27

1-(3,5-Dichloro-pyridin-4-ylmethyl)-4-ethyl-6-methoxy-3,4-dihydro-isoquinoline dihydro-chloride and 1-(3,5-dichloro-pyridin-4-ylmethyl)-4-ethyl-8-methoxy-3,4-dihydro-iso-quinoline dihydrochloride (Compounds 11 and 12)

By working in a way similar to that described in example 5 but using 2-(3,5-dichloro-pyridin-4-yl)-N-[2-(3-methoxy-phenyl)-butyl]-acetamide (3.35 g, 9.12 mmoles), obtained as described in example 26, POCl$_3$ (3.34 ml, 36.5 mmoles) and CH$_3$CN (35 ml), 2.65 g of Compound 11 (yield: 68.8%) and 0.5 g of Compound 12 (yield: 14.5%) were obtained.

a) Compound 11—$^1$H-NMR (DMSO): 12.6(bs,2H); 8.73 (s,2H); 8.12–7.1(m,3H); AB system: Va=5.05, Vb=4.88, Jab=18.4 Hz; 3.93(s,3H); 3.88–3.68(m,2H); 3.08–2.96(m, 1H); 1.63–1.48(m,2H); 0.89(t,3H,JHH=7.4 Hz).

b) Compound 12—$^1$H-NMR (DMSO): 12.8(bs,1H); 8.70(s, 2H); 7.81–7.08(m,3H); AB system: Va=5.01, Vb=4.77, Jab=18.8 Hz; 3.89(s,3H); 3.80–3.63(m,2H); 3.04–2.92(m, H); 1.67–1.43(m,2H); 0.89(t,3H,JHH=7.3 Hz)

EXAMPLE 28

2-(3-Methoxy-phenyl)-4phenyl-butyronitrile

By working in a way similar to that described in example 16 but using 3-methoxy-phenyl-acetonitrile (4.4 g, 30 mmoles), anhydrous DMF (30 ml), NaH (55–65%, 1.44 g, 36 mmoles) and 2-bromoethylbenzene (6.7 g, 36.3 mmoles), 4.8 g of the title compound were obtained (yield: 64%).

$^1$H-NMR (DMSO): 7.37–6.82(m,9H); 3.80(s,3H); 3.73–3.65(m,1H); 2.91–2.69(m,2H); 2.35–2.05(m,2H).

EXAMPLE 29

2-(3-Methoxy-phenyl)-4-phenyl-butylamine

A solution of 2-(3-methoxy-phenyl)-4-phenyl-butyronitrile (4.7 g, 18.7 mmoles), obtained as described in example 28, in anhydrous ethyl ether (50 ml) was dropwise added to a suspension of LiAlH$_4$ (0.71 g, 0.0187 moles) in anhydrous ethyl ether (20 ml) under N$_2$ in a water/ice bath to keep at room temperature. The mixture was kept under N$_2$ for 1 hour at room temperature, then water (0.7 ml), 20% NaOH (0.7 ml) and water again (2.1 ml) were added, the whole was filtered and washed more times with warm ethyl ether. The filtrate was extracted with 10% HCl, the aqueous phase basified with K$_2$CO$_3$, extracted with ethyl ether, anhydnfied and brought to dryness to give 4.4 g of the title compound (yield: 92.1%).

$^1$H-NMR (CDCl$_3$): 7.29–6.73(m,9H); 3.80(s,3H); 3.00–2.76(m,2H); 2.63–1.76(m,5H); 1.08(bs).

EXAMPLE 30

2-(3,5-Dichloro-pyridin-4-yl)-N-[1-(3-methoxy-phenyl)-3-phenyl-propyl]-acetamide A solution of (3,5-dichloro-pyridin-4-yl)-acetic acid (2.06 g, 10 mmoles) and carbonyldiimidazole (1.78 g, 11 mmoles) in THF (30 ml) was kept under stirring for 1 hour under N$_2$. 2-(3-Methoxy-phenyl)-4-phenyl-butylamine (2.55 g, 10 mmoles), obtained as described in example 29, was added and the stirring went on for 1 hour. The mixture was brought to dryness, the residue partitioned between ethyl acetate and aqueous KHSO$_4$. The organic phase was washed with NaHCO$_3$_ and dried. After evaporation to residue, it was obtained an oil which, adsorbed on SiO$_2$ and percolated with ethyl acetate/petrolatum 1:3, gave 4.1 g of the title compound (yield: 92.5%).

$^1$H-NMR (CDCl$_3$): 8.42(s,2H); 7.27–6.64(m,9H) 5.17(bt, 1H); 3.80(s,3H); 3.76(s,2H); 3.75–3.12(m,2H); 2.80–2.65 (m,1H); 2.51–2.43 (m,2H); 2.01–1.79(m,2H).

EXAMPLE 31

3-(3,5-Dichloro-pyridin4-ylmethyl)-7-methoxy-1-phenylethyl-1,4-dihydro-isoluinoline dihydrochloride and 3-(3,5-dichloro-pyridin-4-ylmethyl)-5-methoxy-1-phenylethyl-1,4-dihydro-isoquinoline dihydrochloride (Compounds 13 and 14)

By working in a way similar to that described in example 5 but using 2-(3,5-dichloropyridin-4-yl)-N-[1-(3-methoxy-phenyl)-3-phenyl-propyl]-acetamide (4 g, 9.02 mmoles), obtained as described in example 30, POCl$_3$ (3.3 ml, 36.08 mmoles) and CH$_3$CN (40 ml), 1.84 g of Compound 13 (yield: 40.9%) and 0.59 g of Compound 14 (yield: 14.2%) were obtained.

a) Compound 13—$^1$H-NMR (DMSO): 12.74(bs); 8.73(s, 2H); 8.12–7.11(m,8H); 5.12–4.85(m,2H); 3.93(s,3H); 3.88–3.82(m,2H); 3.22–3.10(m,1H); 2.79–2.53(m,2H); 1.90–1.78(m,2H).

b) Compound 14—$^1$H-NMR (DMSO): 18.71(s,2H); 7.82–7.08(m,8H); 5.07–4.73(m,2H); 3.90(s,3H); 3.82–3.74(m,2H); 3.17–3.05(m,1H); 2.82–2.5 1(m,2H); 1.87–1.74(m,2H).

EXAMPLE 32

Cyclopentyl-(3-methoxy-phenyl)-acetonitrile

By working in a way similar to that described in example 16 but using 3-methoxy-phenyl-acetonitrile (4.4 g, 30 mmoles), anhydrous DMF (30 ml), NaH (55–65%, 1.44 g, 36.3 mmoles) and bromocyclopentane (5.4 g, 36.3 mmoles), 5.8 g of the title compound were obtained (yield: 90%).

¹H-NMR (CDCl₃): 7.29–6.80(m,4H); 3.77(s,3H); 3.79(s, 3H)3.66(s,1H,JHH=7.8 Hz); 2.38–2.18(m,1H); 1.92–1.18 (m,8H).

EXAMPLE 33

2-Cyclopentyl-2-(3-methoxy-phenyl)-ethylamine

By working in a way similar to that described in example 29 but using LiAlH₄ (1.01 g, 26.57 mmoles) in anhydrous ethyl ether (20 ml) and cyclopentyl-(3-methoxy-phenyl)-acetonitrile (5.72 g, 26.57 mmoles), obtained as described in example 32, 5 g of the title compound were obtained (yield: 85.8%).

¹H-NMR (CDCl₃): 7.23–6.71(m,4H); 3.78(s,3H); 3.06–2.76(m,2H); 2.36–2.24(m,1H); 2.06–0.88(m,13H).

EXAMPLE 34

N-[cyclopentyl-(3-methoxy-phenyl)-methyl]-2-(3,5-dichloro-pyridin-4-yl)-acetamide By working in a way similar to that described in example 30 but using (3,5-dichloro-pyridin-4-yl)-acetic acid (2.06 g, 10 mmoles), carbonyldiimidazole (1.78 g, 11 mmoles), THF (30 ml) and 2-cyclopentyl-2-(3-methoxy-phenyl)-ethylamine (2.19 g, 10 mmoles), obtained as described in example 33, 3.8 g of the title compound were obtained (yield: 98.2%), m.p.: 105–106° C.

¹H-NMR (CDCl₃): 8.39(s,2H); 7.19–6.59(m,4H); 5.08 (bs,1H); 3.95–3.02(m,2H); 3.78(s,3H); 3.72(s,2H); 2.49–2.37(m,1H); 2.04–0.87(m,9H).

EXAMPLE 35

1-Cyclopentyl-3-(3,5-dichloro-pyridin-4-ylmethyl)-7-methoxy-1,4-dihydro-isoquinoline dihydrochloride and 1-cyclopentyl-3-(3,5-dichloro-pyridin-4-ylmethyl)-5-methoxy-1,4-dihydro-isoquinoline dihydrochloride (Compounds 15 and 16)

A solution of N-[cyclopentyl-(3-methoxy-phenyl)-methyl]-2-(3,5-dichloro-pyridin-4-yl)-acetamide (3.6 g, 8.84 mmoles), obtained as described in example 34, and POCl₃ (3.24 ml, 35.35 mmoles) in CH₃CN (40 ml) was kept under reflux for 2 hours under N₂, brought to dryness and the residue was taken up with water, neutralised with NaHCO₃ and extracted with CH₂Cl₂. The organic phase was washed brought to dryness and the residue chromatographed (eluent: petrolatum/ethyl acetate 9:1 then 7:3) to give 2 compounds which were salified with HCl/ethyl ether to give 0.46 g of Compound 16 (yield: 12.2%) and a portion of the second compound which was digested with CH₃CN (15 ml), dissolved in water, basified and extracted with ethyl ether. The organic phase was anhydrified and brought to dryness and the residue, dissolved in ethyl ether and salified with HCl/ethyl ether, gave 2.2 g of Compound 15 (yield: 53.8%).

a) Compound 15: ¹H-NMR (DMSO): 12.6(bs,2H); 8.74(s, 2H); 8.17–7.11(m,3H); AB system: Va=5.09, Vb=4.85, Jab=18.4 Hz; 3.93(s,3H); 3.89–3.71(m,2H); 2.92–2.83(m, 1H); 1.95–1.15(m,9H).

b) Compound 16: ¹H-NMR (DMSO): 12.42(bs), 8.73(s,2H); 7.79–7.06(m,3H); 5.10–4.67(m,2H); 3.92(s,3H); 3.84–3.65(m,2H); 2.85–2.74(m, 1H); 1.92–1.14(m,9H).

EXAMPLE 36

2-(3-Methoxy-phenyl)-3-methyl-butyronitrile

By working in a way similar to that described in example 16 but using 3-methoxy-phenyl-acetonitrile (4.4 g, 30 mmoles), anhydrous DMF (40 ml), NaH (55–65%, 1.44 g, 36.3 mmoles) and 2-bromo-propane (4.46 g, 36.3 mmoles), 4.53 g of the title compound were obtained (yield: 79.9%).

EXAMPLE 37

2-(3-Methoxy-phenyl)-3-methyl-butylamine

A solution of 2-(3-methoxy-phenyl)-3-methyl-butyronitrile (4.53 g, 23.93 mmoles), obtained as described in example 36, in ethyl ether (40 ml) was added dropwise to a suspension of LiAlH₄ (1 g, 23.93 mmoles) in ethyl ether (20 ml) under N₂ at room temperature. After 1 hour under stirring the whole was cooled in a water/ice bath and the hydride was decomposed with water (1 ml), 20% NaOH (1 ml) and water (3 ml). The mixture was kept under stirring for 1 hour, filtered, the filtrate washed with water and ether. The organic phase was evaporated to give 4.53 g of the title compound (yield: 47%).

¹H-NMR (CDCl₃): 7.20–6.67(m,4H); 3.77(s,3H); 3.08–2.79(m,2H); 2.31–2.19(m,1H); 1.89–1.71(m,1H); 0.95 and 0.70(2s,6H,JHH=6.4 Hz).

EXAMPLE 38

2-(3,5-Dichloro-pyridin-4-yl)-N-[2-(3-methoxy-phenyl)-3-methyl-butyl]-acetamide

By working in a way similar to that described in example 30 but using (3,5-dichloro-pyridin-4-yl)-acetic acid (4.62 g, 22.4 mmoles), carbonyldiimidazole (4 g, 24.64 mmoles), THF (60 ml) and 2-(3-methoxy-phenyl)-3-methyl-butylamine (4.33 g, 22.4 mmoles), obtained as described in example 37, 8.36 g of the title compound were obtained (yield: 97.9%), m.p.: 94–95° C.

¹H-NMR (CDCl₃): 8.36(s,2H); 7.19–6.54(m,4H); 5.05 (bs,1H); 4.00–3.04(m,2H); 3.77(s,3H); 3.70(s,2H); 2.46–2.30(m,1H); 1.90–1.66(m,1H); 0.98 and 0.68(2d,6H, JHH=6.8 Hz).

EXAMPLE 39

1-(3,5-Dichloro-pyridin-4-ylmethyl)-4-isopropyl-6-methoxy-3,4-dihydro-isoquinoline and 1-(3,5-dichloro-pyridin-4-ylmethyl)-4-isopropyl-8-methoxy-3,4-dihydro-isoquinoline (Compounds 17 and 18)

By working in a way similar to that described in example 5 but using 2-(3,5-dichloropyridin-4-yl)-N-[2-(3-methoxy-phenyl)-3-methyl-butyl]-acetamide (8.1 g, 21.24 mmoles), obtained as described in example 38, POCl₃ (2.54 ml, 27.72 mmoles) and CH₃CN (80 ml), 5.9 g of Compound 17 (yield: 76.5%) and 1.1 g of Compound 18 (yield: 11.4%) were obtained.

a) Compound 17—¹H-NMR (CDCl₃): 8.45(s,2H); 7.56–6.70(m,3H); 4.50–4.10(m,2H); 4.03–3.28(m,2H); 3.85 (s,3H); 2.31–2.22(m,1H); 1.90–1.72(m, 1H); 0.89 and 0.82 (2d,6H,JHH=6.6 Hz).

b) Compound 18—¹H-NMR (DMSO): 8.72(s,2H); 7.83–7.06(m,3H); 5.13–4.72(m,2H); 3.91(s,3H); 3.85–3.64(m,2H); 2.79–2.71(m,1H); 1.89–1.71(m,1H); 0.92 and 0.84(2d,6H,JHH=6.6 Hz).

EXAMPLE 40

1-Methoxy-3-(2-nitro-vinyl)-benzene

Methylamine (8.03M in ethanol, 2.5 ml) and nitromethane (11.8 ml, 0.22 moles) were added to a solution of 3-methoxy-benzaldheyde (27.2 g, 0.2 moles) in methanol (83 ml) and the mixture was kept standing at dark for 72 hours. The resultant precipitate was filtered, washed with methanol and dried to give 15.5 g of the title compound (yield: 43.29%).

$^1$H-NMR (CDCl$_3$): 7.96(d,1H,JHH=13.8 Hz); 7.55(d, 1H); 7.39–7.00(m,4H) 3.83(s,3H).

EXAMPLE 41

1-Methoxy-3-(1-phenyl-2-nitro-propyl)-benzene

A solution of 1-methoxy-3-(2-nitro-vinyl)-benzene (9.3 g, 5.9 mmoles), obtained as described in example 40, in THF (90 ml) was added dropwise to a solution of phenylmagnesium chloride (2N in THF, 38.9 ml, 77.85 mmoles) under N$_2$ at −28° C. and the mixture was kept under stirring for 10 minutes, then 5% HCl (100 ml) was added and the stirring went on for 30 minutes. The phases were separated and the acid one was extracted with ethyl ether and brought to dryness to give a residue which was chromatographed (eluent: petrolatum, then petrolatum/ethyl ether 9:1) to give 6 g of the title compound (yield: 44.9%).

$^1$H-NMR (CDCl$_3$): 7.36–6.75(m,9H); 4.98–4.8 1(m,3H); 3.75(s,3H).

EXAMPLE 42

2-(3-Methoxy-phenyl)-2-phenyl-ethylamine

A mixture of 1-methoxy-3-(1-phenyl-2-nitro-propyl)-benzene (7.8 g, 30.33 mmoles), obtained as described in example 41, ammonium formate (9.56 g, 151.6 mmoles), methanol (80 ml), 10% Pd/C (1.8 g) and 3A molecular sieves (15 g) was kept under reflux for 2 hours, then filtered over celite by washing with methanol and brought to dryness. The residue was taken up with ethyl ether and extracted with 10% HCl. The aqueous phase was basified with K$_2$CO$_3$ and re-extracted with ethyl ether. The organic phase was anhydrified and brought to dryness to give 5.4 g of the title compound (yield: 78.4%).

$^1$H-NMR (CDCl$_3$): 7.33–6.71(m,9H); 3.94(t,1H,JHH=7.4 Hz); 3.76(s,3H); 3.30(d,2H).

EXAMPLE 43

2-(3,5-Dichloro-pyridin-4-yl)-N-[2-(3-methoxy-phenyl)-2-phenyl-ethyl]-acetamide

By working in a way similar to that described in example 4 but using (3.5-dichloro-pyridin-4-yl)-acetic acid (5.15 g, 25 mmoles), carbonyldiimidazole (4.24 g, 26.14 mmoles), THF (75 ml) and 2-(3-methoxy-phenyl)-2-phenyl-ethylamine (5.4 g, 23.76 mmoles), obtained as described in example 42, 8.9 g of the title compound were obtained (yield: 85.7%), m.p.: 142–143° C.

$^1$H-NMR (CDCl$_3$): 8.40(s,2H) 7.31–6.70(m,9H); 5.39(bt, 1H); 4.16–3.81(m,3H); 3.77(s,2H); 3.74(s,3H).

EXAMPLE 44

1-(3,5-Dichloro-pyridin-4-ylmethyl)-6-methoxy-4-phenyl-3,4-dihydro-isoquinoline dihydro-chloride (Compound 19)

A solution of 2-(3,5-dichloro-pyridin-4-yl)-N-[2-(3-methoxy-phenyl)-2-phenyl-ethyl]-acetamide (8.8 g, 0.0212 moles), obtained as described in example 43, and POCl$_3$ (7.76 mg, 0.0848 moles) in CH$_3$CN (100 ml) was kept under reflux under N$_2$ for 3 hours, then brought to dryness and the residue was partitioned between NaHCO$_3$ and ethyl acetate. The organic phase was washed, anhydrified and brought to dryness to give a residue which was taken up with CH$_3$CN and acidified vwith HCl/ethyl ether, then brought to residue. This was crystallised from CH$_3$CN (60 ml) and, after 2 hours in water/ice, was recrystallised from CH$_3$CN (190 ml), then dissolved in water, basified with K$_2$CO$_3$ and extracted with ethyl ether. The solution was brought to dryness and the residue triturated in petrolatum and brought to dryness to give a portion of the compound. The mother liquors were recrystallised and chromatographed to give a furter portion of compound which, joined to the previous one, summed up to 6.12 g of the title compound (yield: 73.8%), m.p.: 136–137° C.

$^1$H-NMR (CDCl$_3$): 8.40(s,2H); 7.31–6.70(m,9H); 5.39 (bt,1H); 4.16–3.81(m,3H); 3.77(s,2H); 3.74(s,3H).

EXAMPLE 45

Trifluoromethanesulphonic acid 2-formyl-6-methoxy-phenyl ester

Triflic anhydride (6.64 ml, 0.0395 moles) was added to a solution of 2-hydroxy-3-methoxy-benzaldheyde (5 g, 0.0329 moles) in CH$_2$Cl$_2$ (50 ml) and pyridine (13.25 ml, 0.164 moles) under N$_2$ at −5–0° C. After 30 minutes the mixture was diluted with CH$_2$Cl$_2$, washed up to acidity with 5% citric acid, water, anhydrified and brought to dryness. The residue was taken up with petrolatum (50 ml) and solidified by cooling with ice, then was filtered by washing with iced petrolatum and dried under vacuum on P$_2$O$_5$ to give 7.52 g of the title compound (yield: 80%).

EXAMPLE 46

2-Cyclopent-1-enylmethyl-3-methoxy-benzaldheyde

A solution of trifluoromethanesulphonic acid 2-formyl-6-methoxy-phenyl ester (6.84 g, 24.06 mmoles), obtained as described in example 45, methylencyclopentane (3.8 ml, 36.08 mmoles), bis(triphenylphosphine)PdCl$_2$ (844.5 mg, 1.203 mmoles), triethylamine (13.39 ml, 96.24 mmoles) in anhydrous DMF (50 ml) was heated at 90° C. under N$_2$ and stirring for 4 days, then poured into water and extracted with ethyl acetate. The organic phase was washed with water, anhydrified and brought to dryness. The residue was flash chromatographed (eluent: petrolaturn/ethyl acetate 98:2) to give 810 mg of the title compound (yield 15%).

$^1$H-NMR (CDCl$_3$): 10.31 and 10.23 (2s,1H); 7.50–7.05 (m,3H); 3.85 and 3.84(2s,3H).

EXAMPLE 47

2-Cylopent-1-enylmethyl-1-methoxy-3-(2-nitro-vinyl)-benzene

Acetic acid (39.66 μl, 0.694 mmoles), methylamine (8.03M in ethanol, 86.42 μl, 0.694 mmoles) and nitromethane (205.2 μl, 3.82 mmoles) were added, under stirring, to a solution of 2-cyclopent-1-enylmethyl-3-methoxy-benzaldheyde (750 mg, 3.47 mmoles), obtained as described in example 46, in methanol (10 ml) and the stirring went on for 28 hours at 40° C. The mixture was brought to dryness and the residue flash chromatographed (eluent: petrolatum/ethyl acetate 7:3) to give 600 mg of the title compound (yield: 67%).

EXAMPLE 48

2-(2-Cyclopent-1-enylmethyl-3-methoxy-phenyl)-ethylamine hydrochloride

A solution of 2-cyclopent-1-enylmethyl-1-metboxy-3-(2-nitro-vinyl)-benzene (0.6 g, 2.31 mmoles), obtained as described in example 47, in anhydrous THF (6 ml) was added dropwise under stirring to a suspension of LiAlH$_4$ (263 mg, 6.93 mmoles) in anhydrous THF (10 ml) under N$_2$. The mixture was kept boiling for 1 hour, then cooled in ice and decomposed with water (0.263 ml), 15% NaOH (0.263 ml) and water (0.789 ml). The mixture was stirred for 1 hour, filtered and evaporated. The residue was dissolved in ethyl acetate, washed with water, dried and acidified with HCl/ ethyl acetate, then evaporated. taken up with ether and crystallised, filtered and dried under vacuum at 40° C. to give 390 mg of the title compound (yield: 63%).

EXAMPLE 49

2-(2-Cyclopentylmethyl-3-methoxy-phenyl)-ethylamine

A solution of 2-(2-cyclopent-1-enylmethyl-3-methoxy-phenyl)-vinylamine (90 mg, 1.46 mmoles), obtained as described in example 48, in methanol (20 ml) was hydrogenated in Parr in the presence of 10% Pd/C (40 mg) for 2 hours. The mixture was filtered and brought to dryness to give 390 mg of the title compound (quantitative yield).

$^1$H-NMR (CDCl$_3$): 8.45(s,1H); 7.13–6.71(m,3H); 3.75(s, 3H); 3.15(s,4H); 2.67(d,2H,JHH=7.4 Hz); 2.08–1.16(m, 9H).

EXAMPLE 50

N-[2-(2-cyclopentylmethyl-3-methoxy-phenyl) ethyl]-2-(3,5-dichloropyridin-4-yl)-acetamide By working in a way similar to that described in example 4 but using (3,5-dichloro-pyridin-4-yl)-acetic acid (356 mg, 1.73 mmoles), carbonyldiimidazole (308 mg, 1.9 mmoles), THF (15 ml), 2-(2-cyclopentylmethyl-3-methoxy-phenyl)-ethylamine (390 mg, 1.44 mmoles), obtained as described in example 49, and triethylamine (0.24 ml, 1.73 mmoles), 520 mg of the title compound were obtained (yield: 86%).

$^1$H-NMR (CDCl$_3$): 8.46(s,2H); 7.09–6.65(m,3H); 5.38 (bs,1H); 3.83(s,2H); 3.78(s,3H); 3.52–3.42(m,2H); 2.86(t, 2H,JHH=6.8 Hz); 2.60(d,2H,JHH=7.4 Hz); 2.05–1.12(m, 9H).

EXAMPLE 51

5-Cyclopentylmethyl-1-(3,5-dichloro-pyridin-4-ylmethyl)-6-methoxy-3,4-dihydro-isoquinoline (Compound 20)

A solution of N-[2-(2-cyclopentylmethyl-3-methoxy-phenyl)-ethyl]-2-(3,5-dichloro-pyridin-4-yl)-acetamide (520 mg, 1.23 mmoles), obtained as described in example 50, and POCl$_3$ (0.236 ml, 2.68 mmoles) in CH$_3$CN (20 ml) under N$_2$ was kept under reflux and stirring for 3 hours, then brought to dryness and the residue dissolved in CH$_2$Cl$_2$, washed with 0.5 N NaOH then with water, anhydrified and brought to dryness. The residue was flash chromatographed (eluent: CH$_2$Cl$_2$/CH$_3$OH 98:2). The fractions containing the compound were brought to dryness and taken up with petrolatum, then evaporated to give a solid which was taken up with petrolatum, filtered and dried under vacuum at 40° C. to give 360 mg of the title compound (yield: 73%).

$^1$H-NMR (CDCl$_3$): 8.45(s,2H); 7.46(d,1H,JHH=8.5 Hz); 6.79(d,1H); 4.3(m,2H); 3.85(s,3H); 3.55–3.45(m,2H); 2.72–2.58(m,4H); 2.08–1.89(m,1H); 1.74–1.11 (m,8H).

EXAMPLE 52

5-Cyclopentylmethyl-1-(3,5-dichloro-pyridin-4-ylmethyl)-6-methoxy-3,4-dihydro-isoquinoline-2-oxide (Compound 21)

To a solution of 5-cyclopentylmethyl-1-(3,5-dichloro-pyridin-4-ylmethNl)-6-methoxy-3,4-dihydro-isoquinoline (310 mg, 0.77 mmoles), obtained as described in example 51, in CH$_2$Cl$_2$ (10 ml), 55% m-chloro-perbenzoic acid (266 mg, 0.85 mmoles) was added. The mixture was kept under stirring for 1 night, then added with further 55% m-chloro-perbenzoic acid (53 mg, 0.3 mmoles). The mixture was diluted with CH$_2$Cl$_2$, washed with a NaHCO$_3$ solution, then with water, anhydrified and brought to dryness. The residue was flash chromatographed (eluent: CH$_2$Cl$_2$ with 3% CH$_3$OH). The eluate was taken up with petrolatum, filtered and dried at 40° C. under vacuum to give 110 mg of the title compound (yield: 34%). m.p.: 176–178° C.

$^1$H-NMR (CDCl$_3$): 12.6(bs,2H); 8.74(s,2H); 8.17–7.11 (m,3H); AB system: Va=5.09, Vb=4.85, Jab=18.4 Hz; 3.93 (s,3H); 3.89–3.71(m,2H); 2.92–2.83(m,1H); 1.95–1.15(m, 9H).

EXAMPLE 53

6-Methoxy-4-phenyl-1-pyridyl-4-ylmethyl-1H-quinolin-2-one (Compound 22)

NaH (605.96 mg, 2.4 mmoles) was added at 55° C. to a suspension of 6-methoxy-4-phenyl-1H-quinolin-2-one (502 mg, 2 mmoles), obtained as described in Chem. Pharm. Bull., 37, 190, (1989), in DMF (9 ml) and the whole was kept under stirring for 45 minutes. Meanwhile, 4-chloro-methyl-pyridine hydrochloride (517 mg, 3.15 mmoles) was partitioned between 10% NaOH and CH$_2$Cl$_2$, the organic phase was washed, anhydrified and brought to dryness at room temperature under vacuum. The resultant oil was taken up with DMF (2 ml) and added to the quinolinone solution. The mixture was kept under stirring at room temperature for 2 hours, then poured into water (50 ml); extracted with ethyl acetate, the organic phase was washed with water, anhydrified and brought to dryness. The residue was chromatographed (eluent: petrolatum/ethyl acetate 1:1) to give 0.19 g of the title compound (yield: 55.5%).

$^1$H-NMR (CDCl$_3$): 8.55–8.52(m,2H); 7.52–7.43(m,5H); 7.16–7.12(m,2H); 7.07–7.01(m,3H); 6.75(s,1H); 5.58 (broad-s,2H); 3.67(s,3H).

EXAMPLE 54

1-(3,5-Dichloropyridin-4-ylmethyl)-6-methoxy-4-phenyl-1H-quinolin-2-one (Compound 23)

6-Methoxy-4-phenyl-1H-quinolin-2-one (1.09 g, 4.35 mmoles), obtained as described in Chem. Pharm. Bull., 37, 190 (1989), was added to a suspension of potassium t-butoxide (0.154 g, 4.58 mmoles) in t-butanol (15 ml) and the mixture was heated at 60° C. for 1 hour, then brought to room temperature and added with 3,5-dichloro-4-chloromethyl-pyridine (0.9 g, 4.58 mmoles). The mixture wvas heated at 60° C. for a night, then poured into water and extracted with ethyl acetate. The organic phase was brought to residue and the solid was chromatographed (eluent: gradient from petrolatum to petrolatum/ethyl acetate 6:4) to give 0.78 g of Compound 23 (yield: 43.6%). m.p.: 191–192° C.

$^1$H-NMR (CDCl$_3$): 8.43(s,2H); 7.52–7.40(m,5H); 7.05–6.93(m,3H); 6.68(s,1H); 5.87(s,2H); 3.67(s,3H).

EXAMPLE 55

Evaluation of the PDE 4 Enzyme Inhibition
a) Purification of Human Polymorphonucleate Leukocytes
The polymorphonucleate leukocytes (PMNs) were isolated from peripheral blood of healthy volunteers according to what described by Boyum A., Scand. J. Immunol., 1976, 5th suppl., 9). Shortly, the isolation of the PMNs was effected by Ficoll-Paque gradient centrifugation followed by sedimentation on dextrane and the erythrocyte contamination was eliminated by hypotonic lysis.

b) PDE 4 Enzyme Purification

The human PMNs were re-suspended in TRIS/HCl buffer (10 mM pH 7.8) containing $MgCl_2$ (5 mM), EGTA (4 mM), mercaptoethanol (5 mM), TRITON-X100 (1%), pepstatin A (1 µM), PMSF (100 µM) and leupeptin (1 µM), and homogenised by Polytron. The homogenate was centrifuged at 25,000×g for 30 minutes at 4° C. and the supernatant was used for the PDE 4 enzyme purification by ion exchange chromatography using the FPLC technique according to what described by Schudt C. et al., Naunyn-Schmidberg's Arch. Pharmacol., 1991, 334, 682. The supernatant was seeded on an UNO Q12 column (Bio-Rad) and the enzyme was eluted by sodium acetate gradient from 50 mM to 1M. The fractions containing enzymatic activity were collected, dialysed against water and concentrated. The resulting PDE 4 enzyme was stored at −20° C. in the presence of ethylenglycole (30% v/v) until the use.

c) PDE 4 Enzyme Inhibition

The enzyme activity was evaluated with an Amersham kit based on the SPA (Scintillation Proximity Assay) technique. The enzymatic reaction was effected in a total volume of 100 µl of TRIS/HCl buffer (50 mM, pH7.5), $MgCl_2$ (8.3 mM), EGTA (1.7 mM), cAMP (1 µM) and [$^3$H]cAMP (~100.000 dpm) as tracer. The compounds of the invention were added at the selected concentrations. The reaction was started by adding the enzyme (15 µg protein/ml), went on for 40 minutes at 30° C. and stopped by adding 50 µl of suspension of SPA particles. The radioactivity due to the particles was measured in a β-emitting counter. The results are expressed as percent activity versus the control present in each experiment. The $IC_{50}$ values were calculated over 9 concentrations equidistant in logarithmic scale using a 4-parameters logistic function by software. The compounds of the present invention showed pharmacologically significant $IC_{50}$ values: for example, Compound 20 gave a value of $IC_{50}$=35.9±4.7 nM.

What is claimed is:

1. A compound of formula I:

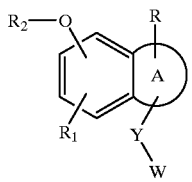

(I)

wherein

A is a 6-membered unsaturated or saturated heterocycle containing a nitrogen atom that may be optionally substituted by an oxo group (=O);

R is:
hydrogen, $(C_{4-7})$cycloalkyl, aryl selected from phenyl, napthyl or indanyl;
$(C_{1-8})$alkyl optionally branched and/or substituted by $(C_{4-7})$ cycloalkyl or aryl selected from phenyl, naphthyl or indanyl;

Y is methylene or ethylene;

W is a heterocycle optionally substituted by a halogen, $(C_{1-4})$alkyl, hydroxy, nitro or carboxy;

$R_1$ is:
hydrogen,
$(C_{4-7})$cycloalkyl or a $(C_{2-8})$alkyl optionally substituted by $(C_{4-7})$cycloalkyl or aryl selected from phenyl, naphthyl or indanyl, or
a heterocycle selected from the group consisting of pyrrole, imidazole, pyrazole, pyridine, pyrazine, pyrimidine, pyridazine, piperazine, triazine, morpholine, pyrrolidine, pyrroline, imidazoline, pyrazoline, pyrazolidine, imidazolidine, piperidine, furan, pyran, isothiazole, isoxazole, and thiophene, wherein $R_1$ may be optionally interrupted by one or more heteroatoms or heterogroups;

$R_2$ is a $(C_{1-6})$alkyl or polyfluoro$(C_{1-6})$alkyl group;

and the N→O derivatives of the compounds of formula I and the pharmaceutically acceptable salts thereof; provided that when Y is methylene and R is hydrogen, $R_1$ is not hydrogen.

2. The compound according to claim 1,
wherein R is
hydrogen,
$(C_{4-7})$cycloalkyl,
aryl selected from phenyl, naphthyl or indanyl,
$(C_{1-8})$alkyl optionally branched and/or substituted by $(C_{4-7})$cycloalkyl or aryl selected from phenyl, naphthyl or indanyl;
$R_1$ is hydrogen, and W is a substituted pyridine.

3. A process for the preparation of a compound according to claim 1 having the structure of a 3,4-dihydroisoquinoline, comprising:
reacting a compound of formula II:

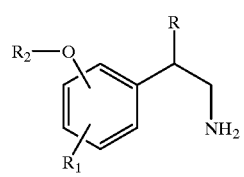

(II)

wherein R, $R_1$, $R_2$ are each as defined in claim 1, with a compound of formula III:

W—Y—Z (III)

wherein W and Y are each as defined in claim 1 and Z is a carboxy group or a reactive derivative thereof,
provided that, when Z is a carboxy group, the reaction occurs in the presence of an activating agent, to give a compound of formula IV:

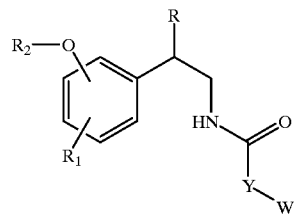

(IV)

wherein $R_1$, $R_2$, R, W and Y are each as defined in claim 1, which is cyclised.

4. A pharmaceutical composition comprising a compound according to claim 1 in admixture with a carrier.

5. A pharmaceutical composition according to claim 4 in a form suitable for parenteral, oral, transdermal, or inhalational administration.

6. A pharmaceutical composition according to claim 5 in the form of a liquid, tablet, capsule, or granulate.

7. A method for inhibiting PDE4 comprising administering an amount of the compound of claim 1 effective to inhibit PDE4.

8. A method for treating a disease or pathology involving PDE4 or TNFα, comprising administering an amount of the compound of claim 1 effective to inhibit PDE4 or TNFα to a subject in need thereof.

9. The method of claim 8, wherein said disease or pathology is an allergic or inflammatory disease.

10. The method of claim 8, wherein said disease or pathology is a respiratory disease.

11. The method of claim 8, wherein said disease or pathology is selected from the group consisting of emphysema, chronic obstructive pulmonary disease (COPD), chronic bronchitis, asthma and allergic rhinitis.

12. The compound of claim 1, wherein R is H.

13. The compound of claim 1, wherein $R_1$ is H.

14. The compound of claim 1, wherein $R_2$ is $(C_{1-6})$alkyl.

15. The compound of claim 1, wherein $R_2$ is polyfluoro $(C_{1-6})$alkyl.

16. The compound of claim 1, wherein Y is methylene.

17. The compound of claim 1, wherein Y is ethylene.

18. The compound of claim 1, wherein W is a heterocycle substituted by a halogen, $(C_{1-4})$alkyl, hydroxy, nitro or carboxy.

19. The compound of claim 1, wherein W is pyridine which may be optionally substituted by a halogen, $(C_{1-4})$alkyl, hydroxy, nitro or carboxy.

* * * * *

UNITED STATES PATENT AND TRADEMARK OFFICE
CERTIFICATE OF CORRECTION

PATENT NO. : 6,358,973 B1
DATED : March 19, 2002
INVENTOR(S) : Napoletano et al.

It is certified that error appears in the above-identified patent and that said Letters Patent is hereby corrected as shown below:

<u>Title page,</u>
Item [22], the PCT information should read:

-- [22]  PCT Filed:  Oct. 1, 1999 --

Signed and Sealed this

Twenty-fourth Day of September, 2002

Attest:

Attesting Officer

JAMES E. ROGAN
*Director of the United States Patent and Trademark Office*